US008272071B2

(12) United States Patent
Kaiser

(10) Patent No.: US 8,272,071 B2
(45) Date of Patent: Sep. 25, 2012

(54) BLINDFOLD FOR AQUATIC GAMES

(76) Inventor: Karl Kaiser, Rossmoor, CA (US)

(*) Notice: Subject to any disclaimer, the term of this patent is extended or adjusted under 35 U.S.C. 154(b) by 0 days.

(21) Appl. No.: 12/573,345

(22) Filed: Oct. 5, 2009

(65) Prior Publication Data
US 2010/0199411 A1 Aug. 12, 2010

Related U.S. Application Data

(60) Provisional application No. 61/102,720, filed on Oct. 3, 2008, provisional application No. 61/120,778, filed on Dec. 8, 2008.

(51) Int. Cl.
A61F 9/00 (2006.01)
(52) U.S. Cl. ........................................ 2/15; 2/440; 2/426
(58) Field of Classification Search .................. 132/208, 132/270, 274, 333; 351/158, 175, 240, 46, 351/172, 183, 41, 154, 44, 83, 86, 177, 43, 351/45, 203, 51, 156; 367/7, 901, 131, 118; 356/908; 600/437, 471; 128/858, 915, 916; 2/452, 434, 442, 430, 447, 428, 441, 443, 2/436, 439, 440, 435, 433, 432, 431, 426, 2/15, 425, 424, 422, 410, 427
See application file for complete search history.

(56) References Cited

U.S. PATENT DOCUMENTS

| 1,886,725 | A | * | 11/1932 | Pedersen | 604/308 |
| 1,935,634 | A | * | 11/1933 | Lves | 2/440 |
| 2,537,768 | A | * | 1/1951 | Laporte | 2/15 |
| 2,874,385 | A | * | 2/1959 | Wade | 2/15 |
| 3,541,608 | A | * | 11/1970 | Otwell | 2/15 |
| 3,606,648 | A | * | 9/1971 | Schuler | 24/16 PB |
| 4,520,510 | A | * | 6/1985 | Daigle | 2/452 |
| 4,649,908 | A | * | 3/1987 | Ghaly | 128/858 |
| 4,790,031 | A | * | 12/1988 | Duerer | 2/439 |
| 5,093,940 | A | * | 3/1992 | Nishiyama | 2/441 |
| 5,309,577 | A | * | 5/1994 | Buononato et al. | 2/452 |
| 5,425,380 | A | * | 6/1995 | Hudson et al. | 128/858 |
| 5,555,571 | A | * | 9/1996 | McCaffrey | 2/428 |
| 6,098,206 | A | * | 8/2000 | Chou | 2/428 |
| 6,826,784 | B2 | * | 12/2004 | Patire | 2/433 |
| 6,907,617 | B2 | * | 6/2005 | Johnson | 2/13 |
| 2004/0163163 | A1 | * | 8/2004 | Shiue | 2/428 |
| 2004/0218140 | A1 | * | 11/2004 | Bleau | 351/92 |
| 2005/0022823 | A1 | * | 2/2005 | Davison et al. | 128/858 |
| 2005/0034224 | A1 | * | 2/2005 | Shiue | 2/428 |
| 2006/0048288 | A1 | * | 3/2006 | Haslbeck | 2/439 |
| 2007/0017007 | A1 | * | 1/2007 | McBride | 2/426 |
| 2008/0068556 | A1 | | 3/2008 | Harrison | |

* cited by examiner

Primary Examiner — Khao Huynh
Assistant Examiner — Khaled Annis
(74) Attorney, Agent, or Firm — Knobbe, Martens, Olson & Bear LLP

(57) ABSTRACT

An eye cover for use in an aquatic environment is provided. In certain embodiments, the eye cover comprises an elastic headband configured to be worn around a wearer's head and configured in use to cover or surround the wearer's eyes. The elastic headband can be configured to provide an at least water-resistant seal around the wearer's eyes. At least one eye chamber disposed on a surface of the headband that in use faces the wearer's eyes can further be provided. The at least one eye chamber permit the wearer's eyes to remain open when the headband covers the wearer's eyes. The at least one eye chamber comprises a flange extending from the headband, wherein the flange is configured to provide at least a water-resistant seal around the wearer's eye.

7 Claims, 11 Drawing Sheets

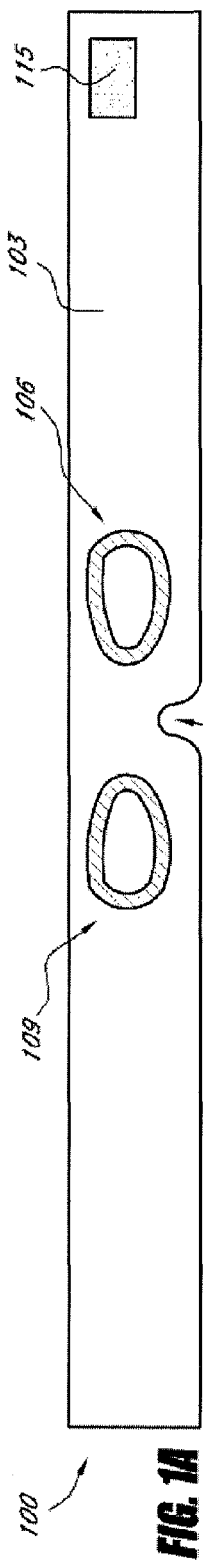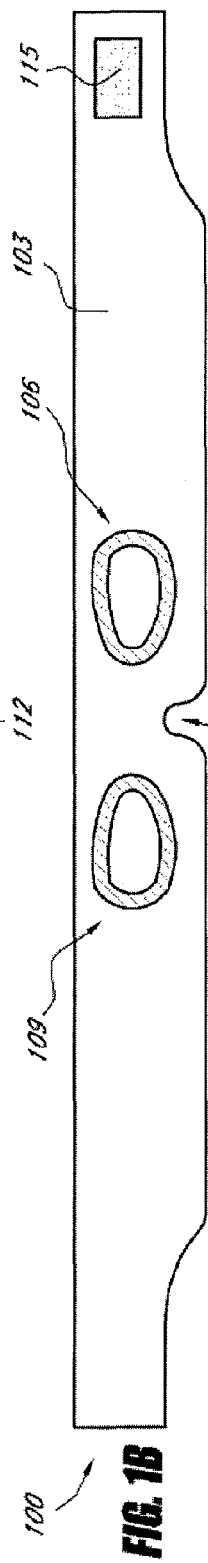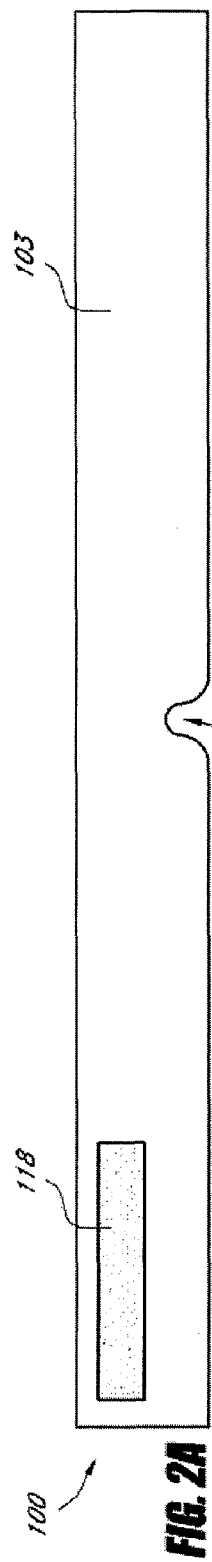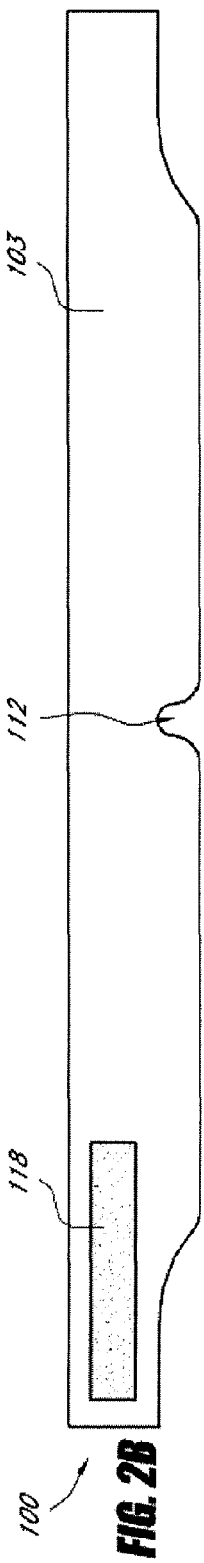

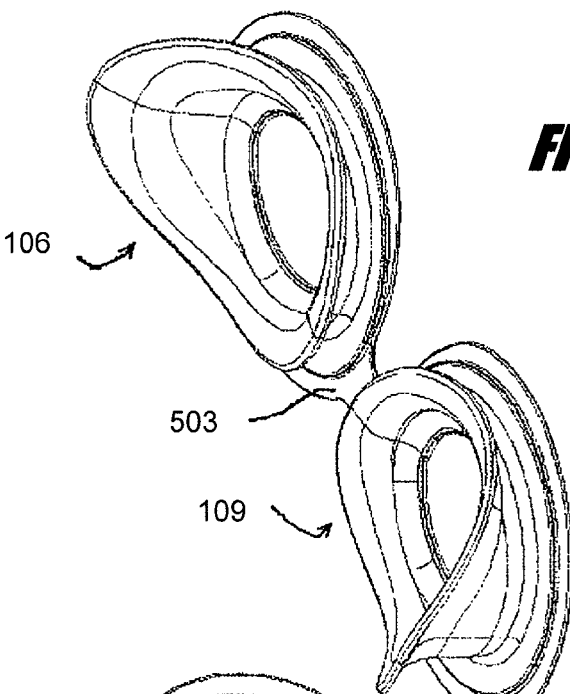
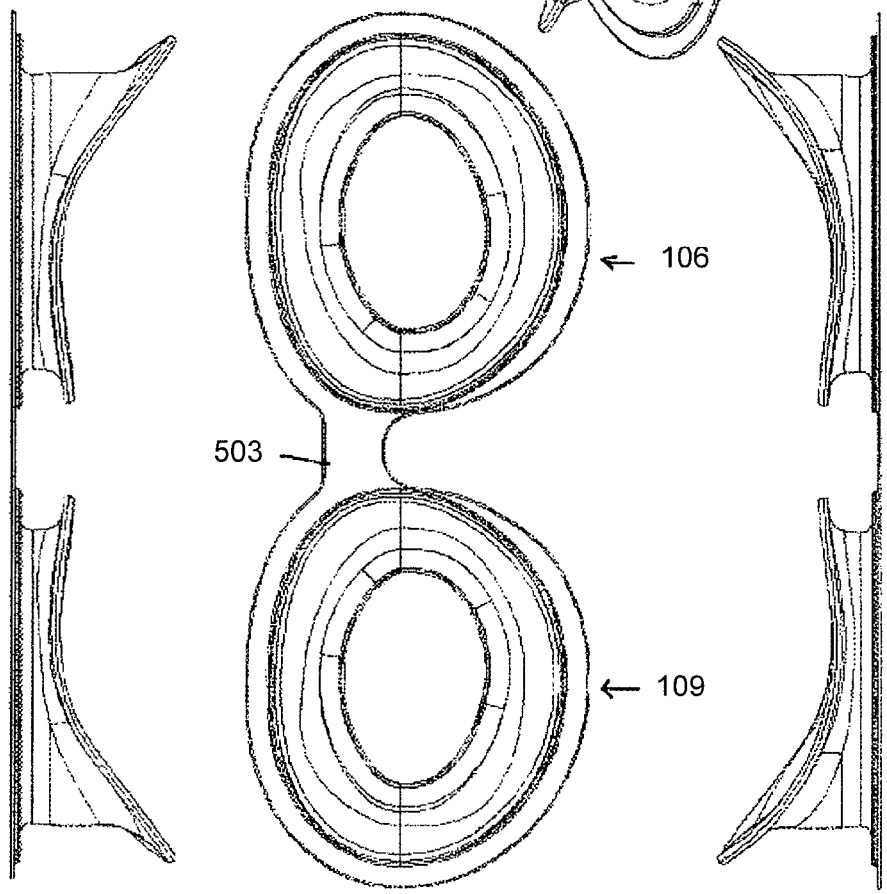
FIG. 5D
FIG. 5B  FIG. 5A  FIG. 5C

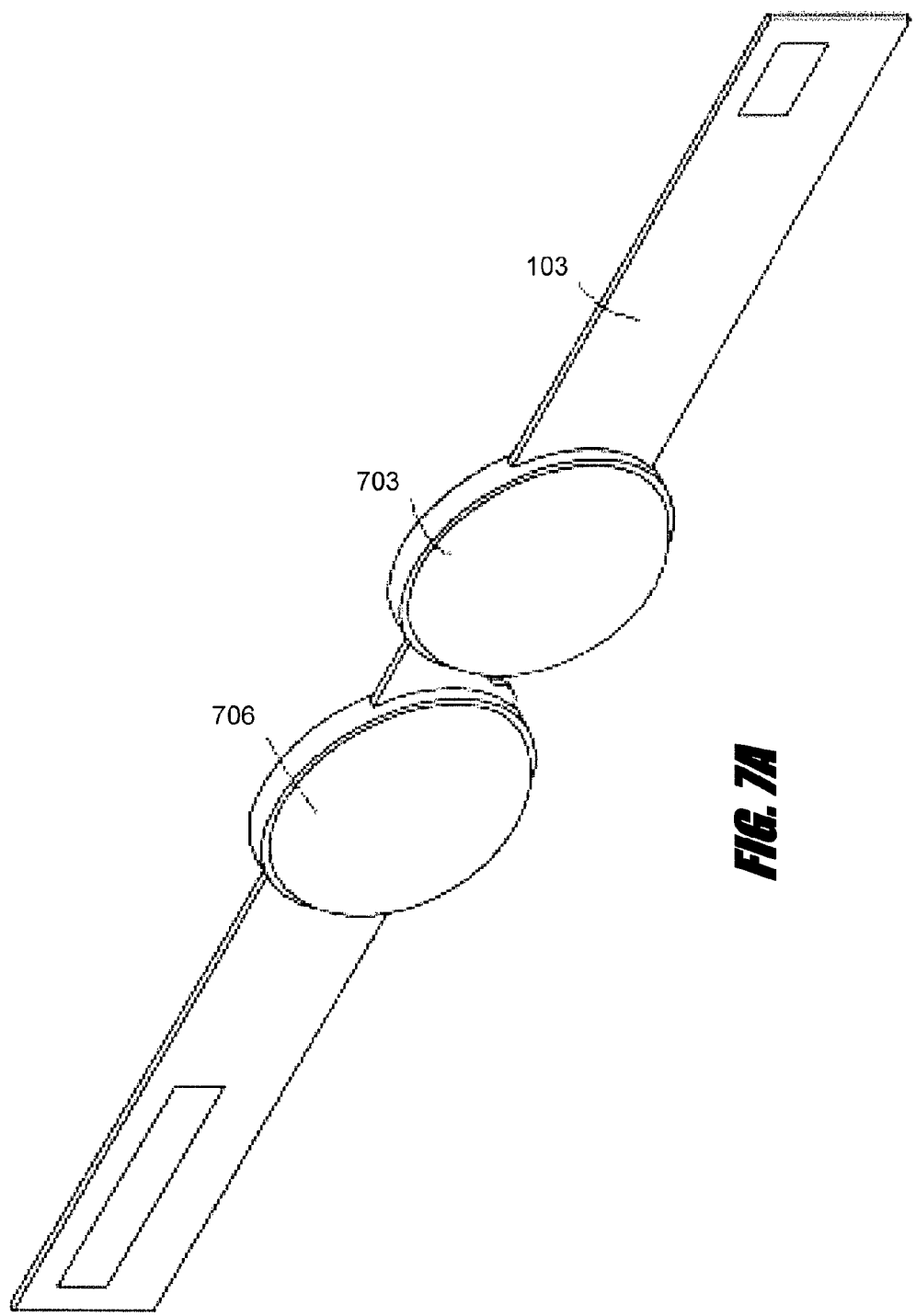

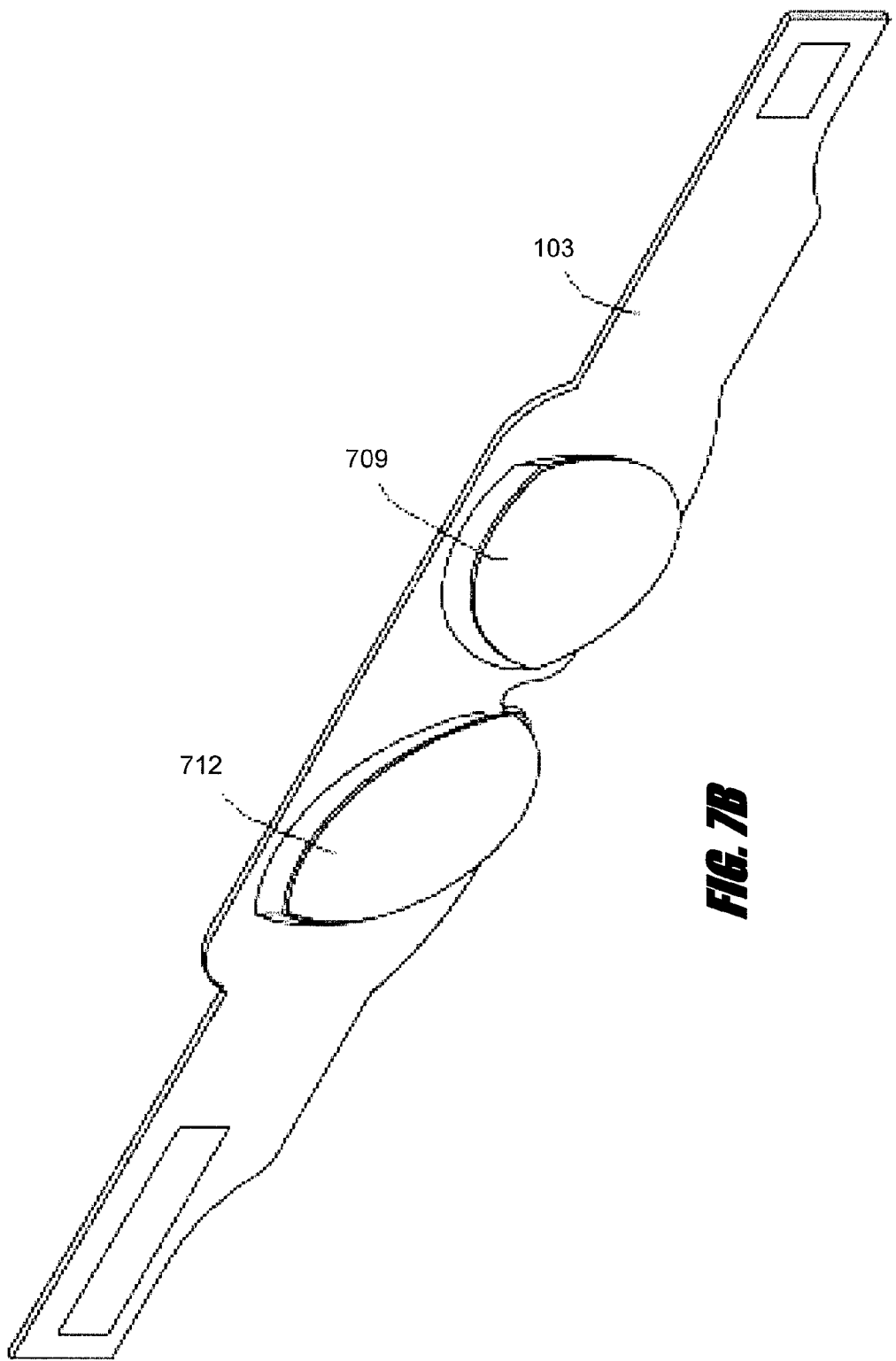

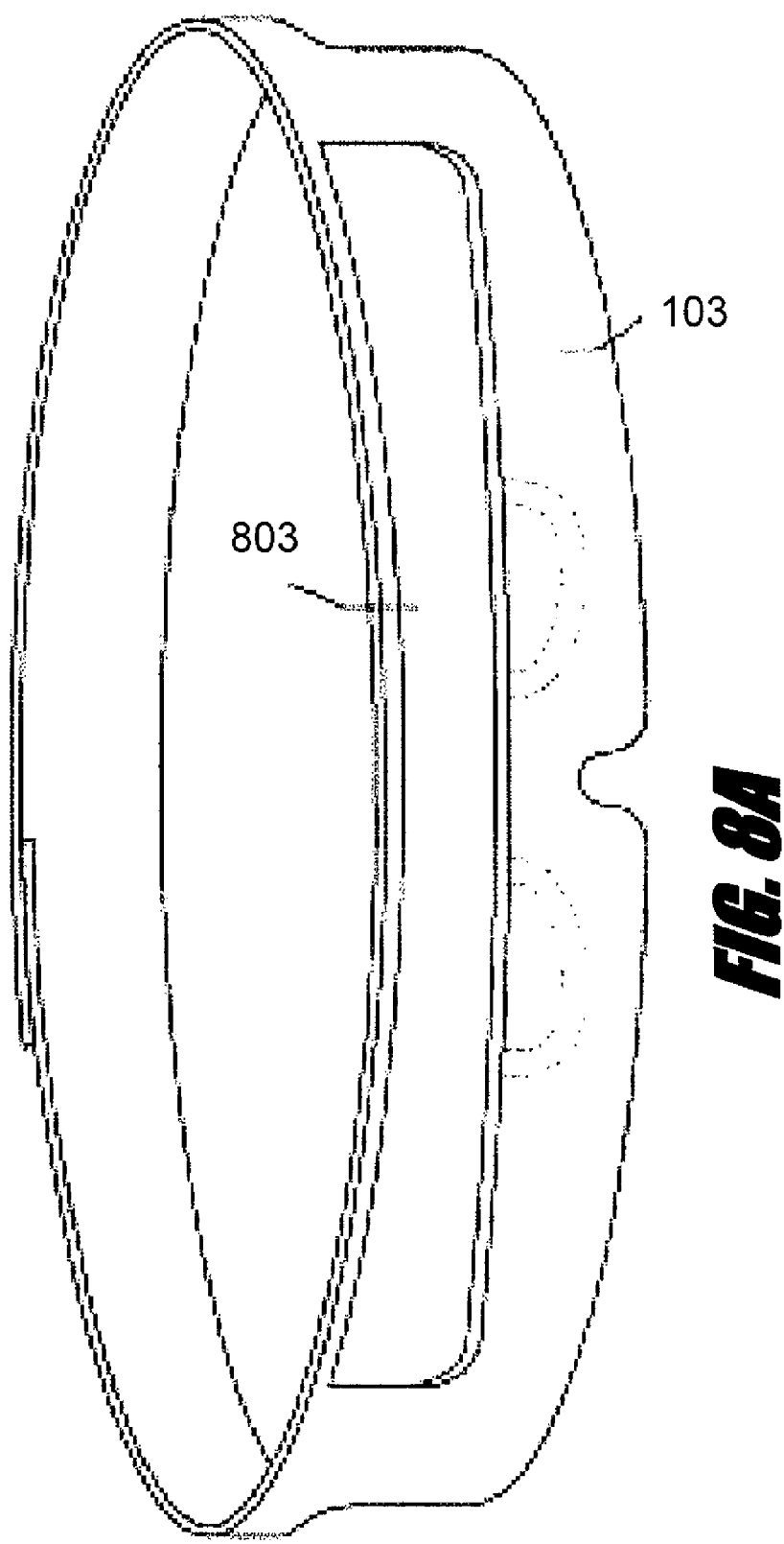

BLINDFOLD FOR AQUATIC GAMES

RELATED APPLICATIONS

This application claims the benefit of U.S. Provisional Patent Application No. 61/102,720, titled "AQUATIC EYE COVER APPARATUS AND METHOD," filed on Oct. 3, 2008, and U.S. Provisional Patent Application No. 61/120,778, titled "AQUATIC EYE COVER APPARATUS AND METHOD," filed on Dec. 8, 2008, the entire contents of both of which are incorporated herein by this specific reference.

BACKGROUND

1. Technical Field

This disclosure relates generally to eye covers and more specifically to eye covers for use in aquatic environments.

2. Description of the Related Art

For various reasons, eye covers for use in aquatic environments, such as masks and goggles, are popular swim accessories. Conventional eye covers have a number of drawbacks, however, because they are easy to dislodge or displace during aquatic activities.

For example, these eye covers are not well suited to "blind tag" variants that require that certain players not be allowed to see or view the other players. Certain blind tag variants such as "Marco Polo" are played in a swimming pool. In Marco Polo, the It player(s) must sense where the other players are by sound. At any time, the It player(s) may call out "Marco!," and all the other players are required to yell "Polo!" in response. Based on the sounds of the other players' responses, the It player(s) can determine the other players' locations. When an It player succeeds in tagging another player, the latter becomes It.

A difficulty with blind tag variants, including blind tag variants played in a swimming pool, is ensuring that the It player is not able to see or view the other players. The prior art has attempted to improve playing of blind tag variants in a swimming pool by providing goggles or a mask comprising a lens element effective to distort images. Other prior art has attempted to improve game play by providing goggles or a mask with a screen such as aluminum foil or duct tape between the eye and the lens element to obscure or block the It player's vision. However, these solutions do not prevent an It player from peeking at the other players by adjusting, dislodging, or displacing the goggles' or the mask's placement. Furthermore, a screen placed between the eye and the lens element can be a safety hazard if the screen becomes dislodged during game play. Accordingly, a need remains for eye coverings suitable for use in aquatic environments that are not readily dislodged or displaced.

SUMMARY

In various embodiments, eye covers for use in aquatic environments and methods for manufacturing such eye covers are disclosed herein. The eye covers have improved stability during swimming or other aquatic game play and resist dislodgment and displacement. The eye covers can comprise a wide, preferably one-piece, preferably elastic headband that is configured to be worn around the circumference of a wearer's head. The headband can be configured to be pulled around the wearer's head, such that the headband is positioned over the wearer's eyes. The headband can also be configured to be wrapped around the wearer's head. The eye covers can also comprise a covering system and an overlay configured to cover at least a portion of the covering system In at least one embodiment, a blindfold for use in an aquatic environment is provided. The blindfold comprises a elastic headband configured to be worn around a wearer's head and configured in use to cover the wearer's eyes, wherein the elastic headband is configured to provide an at least water-resistant seal around the wearer's eyes. At least one eye chamber is disposed on a surface of the headband that in use faces the wearer's eyes. The at least one eye chamber is configured to permit the wearer's eyes to remain open when the headband covers the wearer's eyes. Each of the at least one eye chamber can comprise a flange extending from the headband, wherein the flange is configured to provide at least a water-resistant seal around the wearer's eye.

In at least one embodiment, an eye cover for use in an aquatic environment is provided. The eye cover comprises a headband configured to be worn around the circumference of a wearer's head. The headband can comprise one or two cutout regions. One or two eye chambers can be inserted through the cutout regions or disposed over the cutout regions. The one or two eye chambers are configured in use to cover the wearer's eyes. The one or two eye chambers can form in use a watertight seal around a wearer's eyes.

In the above-described embodiments, the headband can be configured to be pulled around the wearer's head, such that the headband is positioned over or around the wearer's eyes. The headband can also be configured to be wrapped around the wearer's head. The headband can be secured around a wearer's head by Velcro, a snap, a grommet, or the like.

The headband can comprise a sealing fabric or material that is configured to provide the at least water-resistant seal around the wearer's eyes. The sealing fabric or material can be neoprene, plastic, vinyl, or the like. An outer edge of the headband can be folded over to provide the at least water-resistant seal around the wearer's eyes. The headband can comprise at least one sealing structure disposed on the surface of the headband that in use faces the wearer's eyes, wherein the sealing structure is configured to provide the at least water-resistant seal around the wearer's eyes. The sealing structure can comprise a waterproof bead or strip.

The at least one eye chamber can further comprise a gasket disposed on a surface of the flange that in use contacts the wearer's face. The gasket can be configured in use to provide a watertight seal around a wearer's eye.

At least one eye chamber can further comprise a rigid or semi-rigid lens that covers the flange and is disposed proximal the headband. In embodiments comprising two eye chambers, the two eye chambers can be connected by a bridge.

The eye cover can further comprise one or more rigid or semi-rigid projections disposed on a surface of the headband that in use faces outward, configured to facilitate removal of the headband.

In at least one embodiment, a method for manufacturing an eye cover for use in an aquatic environment is provided. The method comprises securing at least one eye chamber to an elastic headband configured to be worn around a wearer's head and configured in use to cover the wearer's eyes. In embodiments with two eye chambers, the method can further comprise attaching each eye chamber to a bridge prior to securing the eye chambers to the elastic headband.

In another embodiment, a method for blindfolding a person is provided. The method comprises providing swim goggles or a mask and pulling a skirt over the goggles or mask, wherein the skirt comprises a cord disposed in the skirt's periphery. The method further comprises tightening the cord to secure the skirt to the goggles or mask. The act of tightening can comprise sliding a barrel lock on the cord to shorten the cord's effective diameter.

For purposes of summarizing the embodiments and the advantages achieved over the prior art, certain items and advantages are described herein. Of course, it is to be understood that not necessarily all such items or advantages may be achieved in accordance with any particular embodiment. Thus, for example, those skilled in the art will recognize that the inventions may be embodied or carried out in a manner that achieves or optimizes one advantage or group of advantages as taught or suggested herein without necessarily achieving other advantages as may be taught or suggested herein. Processes and methods described herein do not imply a fixed order to the steps, and embodiments may be practiced in any order that is practicable.

BRIEF DESCRIPTION OF THE DRAWINGS

The drawings and the associated descriptions are provided to illustrate embodiments and not to limit the scope of the disclosure. Throughout the drawings, reference numbers are re-used to indicate correspondence between referenced elements. In addition, the first digit of each reference number indicates the figure in which the element first appears.

FIG. 1A is a back plan view of an example eye cover.

FIG. 1B. is a back plan view of another example eye cover.

FIG. 2A is a front plan view of the eye cover according to FIG. 1A.

FIG. 2B is a front plan view of the eye cover according to the second embodiment of FIG. 1B.

FIG. 5A through FIG. 5E show two example eye chambers. FIG. 5A is a bottom-up view of the eye chambers. FIG. 5B and FIG. 5C are side-plan views of the eye chambers. FIG. 5D is a perspective view of the eye chambers. FIG. 5E is a rear perspective view of example eye chambers connected by an adjustable bridge.

FIG. 7A is a front perspective view an example eye cover comprising two shells. FIG. 7B is a front perspective view of another example eye cover comprising two shells.

FIG. 8A is a front perspective view of an example eye cover comprising a handle.

These and other features will now be described with reference to the drawings summarized below. These drawings and the associated description are provided to illustrate preferred embodiments of the invention and not to limit the scope of the invention.

DETAILED DESCRIPTION

Various embodiments include the realization that swimming or aquatic game play can be improved by providing a water resistant or watertight blindfold over a wearer's eyes. Still further, various embodiments including the realization that game play of blind tag variants in an aquatic environment can be improved by providing a blindfold that obscures a wearer's vision while permitting the wearer to keep her or his eyes open underwater. Still further, various embodiments include the realization that a wide headband disposed around the circumference of a wearer's head can improve the stability of an eye cover during swimming or aquatic game play. Still further, various embodiments include the realization that swimming and aquatic game play can be improved by providing an eye cover with at least two mechanisms of sealing against water. These are other realizations are discussed in more detail below.

Watertight and water resistant eye covers and methods of making watertight and water resistant eye covers are provided. As used herein, "watertight" is defined to mean fitted to be substantially impervious to penetration of water under ordinary use or game play; "water resistant" is defined to mean constructed or fitted to be substantially resistant to the penetration of water under ordinary use or game play. Various waterproof, water resistant, and water permeable construction materials, as described in more detail below, are used to facilitate a watertight or water-resistant fit. "Waterproof" is defined to mean constructed to be substantially impervious to penetration of water under ordinary use or game play; "water permeable" is defined to mean constructed to permit penetration of water under ordinary use or game play. In some embodiments, a headband with one or more eye chambers comprising a flange and/or gasket is employed to facilitate a watertight fit around a wearer's eyes. A "flange" is a projecting rim or collar disposed on or through a headband. A "gasket" is a ring or liner disposed on the flange configured to facilitate a water resistant or watertight fit between the flange and the skin around the wearer's eyes.

For a more detailed understanding of the disclosure, reference is first made to FIG. 1A, which shows an example embodiment of an eye cover 100. The eye cover 100 comprises a headband 103.

Figure 3:
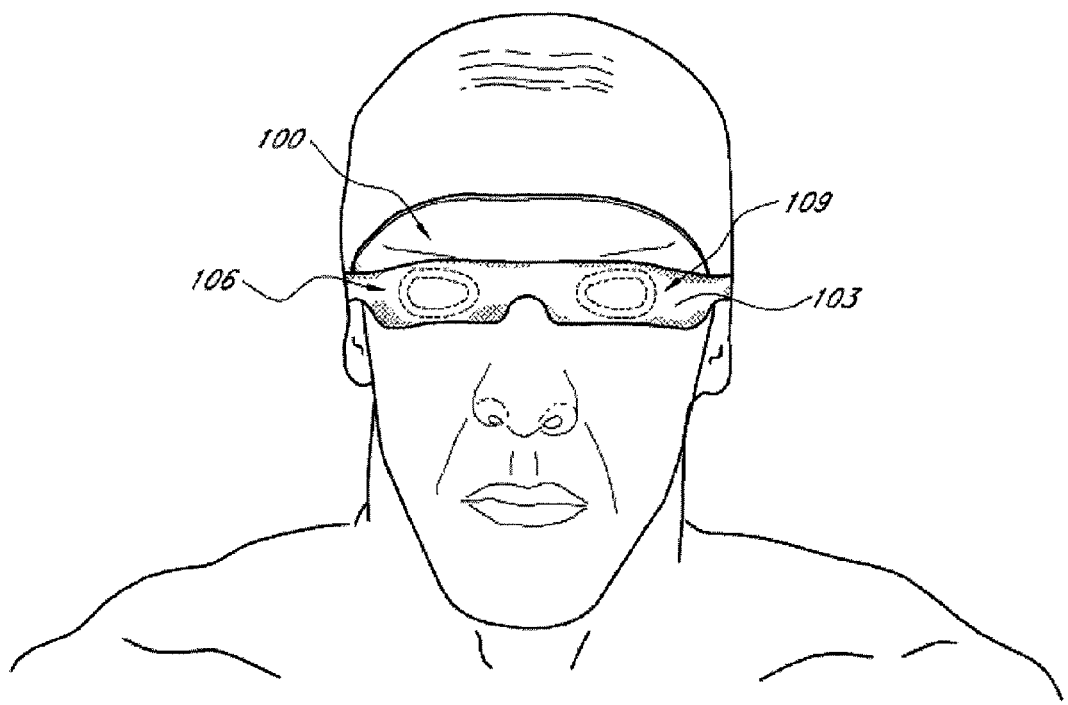
FIG. 3 is a front perspective view of an example eye cover in use by a wearer.

In use, the headband 103 is positioned around a wearer's head. A portion of the headband 103 can cover or surround the wearer's eyes, as demonstrated by the example positioning of FIG. 3. The headband 103 can be flexible. In certain preferred embodiments, at least a portion of the headband 103 is elastic (that is, springy or stretchy). An elastic headband 103 can advantageously provide a snug fit around the wearer's head, facilitating a water-resistant or water tight fit. An elastic headband 103 can also provide more comfort for the wearer.

Referring again to FIG. 1A, a variety of construction materials are suitable for the headband 103. Suitable materials include natural materials such as natural latex, natural rubber, and natural fibers, as well as and synthetic materials such as synthetic latex, synthetic rubber, silicone, polyester, synthetic fibers, spandex, neoprene, and nylon. In addition, other polymeric materials can be used as suitable construction materials. In various embodiments, a headband 103 comprises a combination of natural materials, a combination of synthetic materials, or a combination of natural and synthetic materials. Preferably, the construction material is selected to be resistant to deterioration by chlorine or other chemicals in water. For instance, synthetic polymers such as silicone and neoprene resist deterioration by chlorine.

In certain embodiments, the headband 103 construction material is selected to render the headband 103 water permeable, water resistant, or waterproof. Preferably, however, the headband 103 construction material is selected to be water resistant or waterproof. Furthermore, the headband 103 thickness can be selected to facilitate water resistance or water tightness. In one embodiment, the headband 103 thickness is between about 1 and 10 mm, and more preferably between about 1 and 5 mm, and most preferably between about 2 and 4 mm. The headband 103 height is preferably wide. In one embodiment, the headband height is about 160 mm or less, about 120 mm or less, or about 100 mm or less at its widest dimension (e.g., not including any optional tapering in the nasal or ear regions). In certain embodiments, the minimum height (e.g., around the nose or ears regions) is about 100 mm or less, about 75 mm or less, or about 50 mm or less, or about 30 mm or less. A wide headband 103 advantageously provides greater stability to an eye cover 100 during swimming or aquatic game play. The larger surface area also advantageously permits designs or patterns to be emplaced on the outward-facing surface of the headband 103 via screen printing or other suitable methods.

The headband 103 can be configured to provide a water-resistant or, more preferably, a waterproof seal around at least a portion of the wearer's face. For example, the headband 103 construction material and/or thickness can be selected to provide a waterproof seal around the wearer's eyes. Accordingly, the headband 103 can comprise a material selected to provide a water-resistant or water-tight seal where the material contacts the wearer's skin. Preferably, in use, the headband 103 is worn around a wearer's head and covers the wearer's eyes. The headband 103 material can form a substantially water-tight seal where the headband 103 contacts the skin on the wearer's face. Rubber, neoprene, silicone, plastic, epoxy, latex, urethane, vinyl, and the like are examples of materials that can form a substantially watertight seal when placed against skin. For example, the headband 103 can be formed from a stretchy neoprene.

The headband 103 can also comprise a combination of water permeable, and/or waterproof materials. For example, the portion of the headband 103 covering the wearer's eyes can be constructed of waterproof material(s) while the remainder of the headband 103 can comprise water permeable and/or water resistant construction materials.

In at least one embodiment, a portion of the headband 103 that in use covers the wearer's eyes, such as the inner surface of the headband 103, can be formed of neoprene or other suitable material such as plastic, vinyl, etc., as described above. In other embodiments, the inner surface of the headband 103 that covers the wearer's eyes can be treated with a sealant material such as epoxy, latex, or urethane. The remainder of the headband 103 can be formed of another material. Thus, a watertight seal around the wearer's eyes can be provided by the epoxy, latex, urethane, or other sealant treatment.

Other techniques for providing a water-resistant or waterproof seal around a portion of the wearer's face are also suitable. For instance, at least a portion of the headband 103 material can be shaped, molded, or otherwise formed to create a water-resistant or watertight seal. In at least one embodiment, a portion or edge of the headband 103 material can be arched or folded over to create an o-ring-type seal. The arched or folded material can be sewn, glued, or otherwise secured in place. The resulting o-ring-type seal can be water-resistant or watertight.

Preferably, the shaped, molded, or otherwise formed portion of the headband 103 comprises at least one material with sealing properties. For example, the portion of the headband 103 that in use covers the wearer's eyes can be formed of neoprene or other suitable material such as plastic, vinyl, etc. The neoprene, plastic, vinyl, etc. portion can be arched or folded over to form a watertight seal around the wearer's eyes. In certain embodiments, the formed portion is about 1 inch in width, about ¾ inch in width, or about ¼ inch in width. Preferably, the formed portion is about ½ inch in width.

In certain embodiments, one or more sealing structures can be glued, sewn, embedded, integrated, or otherwise attached to the headband 103 to provide at least a water-resistant seal around at least a portion of the wearer's face. The sealing structure can be configured to contact the skin and seal out water. For instance, a bead or strip of latex or urethane can be glued or applied on a portion of a headband 103 that in use surrounds a wearer's eyes and/or nose. A variety of other sealing structures can also be used alone or in combination. For example, at least one of the sealing structures can comprise an inflatable bladder, a cushion, or the like. As another example, at least one of the sealing structures comprises an adhesive strip.

The one or more sealing structures can be attached to a portion of the headband 103, such that in use, the structure(s) surround the wearer's eyes. As an example, the one or more sealing structures can be attached to the headband 103 near an outer edge of the headband 103. In certain embodiments, the one or more sealing structures are about 1 inch in width, about ¾ inch in width, or about ¼ inch in width. Preferably, one or more of the sealing structures is about ½ inch in width. In certain embodiments, the one or more of the sealing structures is between about ⅛ inch and ½ inch thick, for example, about ¼ inch thick.

The headband 103 or the portion of the headband 103 that covers the wearer's eyes can be configured to be substantially opaque to light or at least light-resistant. For example, at least the portion of the headband 103 covering the wearer's eyes can be constructed from thick, dark, and/or dense construction materials, lined with an opaque liner, etc. In addition, the headband 103 thickness can be selected to inhibit the passage of light. In various embodiments, the amount of light that passes through the construction materials can be reduced, for example, by 25%, 50%, 75%, 90%, or 100%. A light-resistant portion preferably permits some light to pass therethrough but does not permit a wearer to discern images. A material that is light resistant, for example, can be constructed of a material comprising pinhole apertures. A light-resistant portion can advantageously be worn by a wearer who is afraid of the dark. In certain embodiments, at least a portion of the headband 103 can be transparent to light.

As shown in FIG. 1A, in certain embodiments, the headband 103 can comprise a nose notch 112 to accommodate the shape of a wearer's nose. In certain embodiments, the nose notch 112 is located at or near the middle of the headband 103. The provision of a nose notch 112 can advantageously provide comfort for the wearer and/or assure that the wearer's nasal passages do not become compressed. In certain embodiments, the nose notch 112 can be pre-formed in the headband 103 during manufacture. In certain embodiments, the construction material of the headband 103 can be cut or shaped by the wearer to create or form a nose notch 112.

In certain embodiments, the headband 103 can cover all or part of the nose. In at least one embodiment, the headband 103 comprises an integrated noseplug. In one embodiment, the headband 103 provides a watertight seal around a wearer's nostrils. The provision of a headband that covers all or part of the nose (for example, with an integrated noseplug) advantageously provides greater comfort for wearers that wish to prevent water from entering their nasal passages.

As shown in FIG. 1A and FIG. 2A, the headband 103 can have a substantially rectangular shape. In certain embodiments, the headband 103 can have a continuous ring shape. In those embodiments in which the headband 103 has a continuous ring shape, a wearer positions the headband 103 by pulling the headband 103 over the head and over the eyes. In certain embodiments, the headband 103 is about 30 inches in length or circumference, preferably about 26 inches in length or circumference, more preferably about 24 inches in length or circumference, and most preferably about 22 inches in length or circumference.

As shown in FIG. 1B and FIG. 2B, the headband 103 height can have a tapered or otherwise irregular shape. For example, the headband 103 height can be narrower around the portion that in use is proximate the wearer's ears or nose. A tapered shape that avoids covering a wearer's ears during use can advantageously improve the wearer's hearing while playing Marco Polo. A tapered shape around the nose (a nose notch) can accommodate wearers who prefer to swim with their nasal passages uncovered.

In various embodiments, the edges of the headband 103 can comprise an attachment mechanism. As shown in FIG. 1A, in a preferred embodiment, the loop or hook side of a first Velcro attachment 115 or a snap can be attached, molded, embedded, integrated, or otherwise formed at one end of the headband 103, preferably on the side that in use faces inward. As shown in FIG. 2A, the compliant side of the Velcro attachment 118 or a compliant snap is attached, molded, embedded, integrated, or otherwise formed at the opposite end of the headband 103, preferably on the side that in use faces outward. To join the edges, the wearer overlaps and joins the two sides of the Velcro attachments 115, 118 or snaps. In certain embodiments, both the first and second Velcro attachment 115, 118 or other attachment mechanism are located on the same side of the headband 103.

Preferably, the length of at least one of the side of Velcro is selected to allow the headband 103 to be adjusted snugly around head or face. For example, as shown in FIG. 2A, the second Velcro attachment 118 is selected to be longer than the first Velcro attachment 115 shown in FIG. 1A, permitting the headband 103 to fit snugly around various head circumferences. In certain embodiments, at least one of the Velcro attachments 115, 118 is about four inches long or about eight inches long. Most preferably, at least one of the Velcro sides is about six inches long.

Other attachment mechanisms are suitable for use in securing the headband 103 around the wearer's head. Attachment mechanisms can include, but are not limited to buttons, grommets, adjustable tabs, brackets, etc. In certain embodiments, the two edges of a headband 103 can be tied together.

Referring again to FIG. 1A, in various embodiments, an eye cover 100 can comprise a headband 103 and one or more eye chambers 106, 109 that are attached to, molded to, embedded in, integrated in, glued on, sewn into, or otherwise formed to the headband 103. In certain embodiments, an eye chamber 106, 109 is attached to the headband 103 with glue or other adhesive. In other embodiments, the eye chambers 106, 109 are heat molded to the headband 103. In other embodiments, the headband 103 retains the eye chambers, for example, with flaps, strips, or portions of fabric. Alternatively, the eye chamber(s) 106, 109 and the headband 103 can be a unitary construction.

The eye chambers 106, 109 are preferably waterproof and in use watertight, so as to stop water from touching a wearer's eyes. A watertight fit can be enhanced in use by the action of water pressure pushing the eye chambers 106, 109 against the region surrounding the wearer's eyes. In certain embodiments, an eye cover comprises a single eye chamber that in use covers both eyes.

Figure 4A:
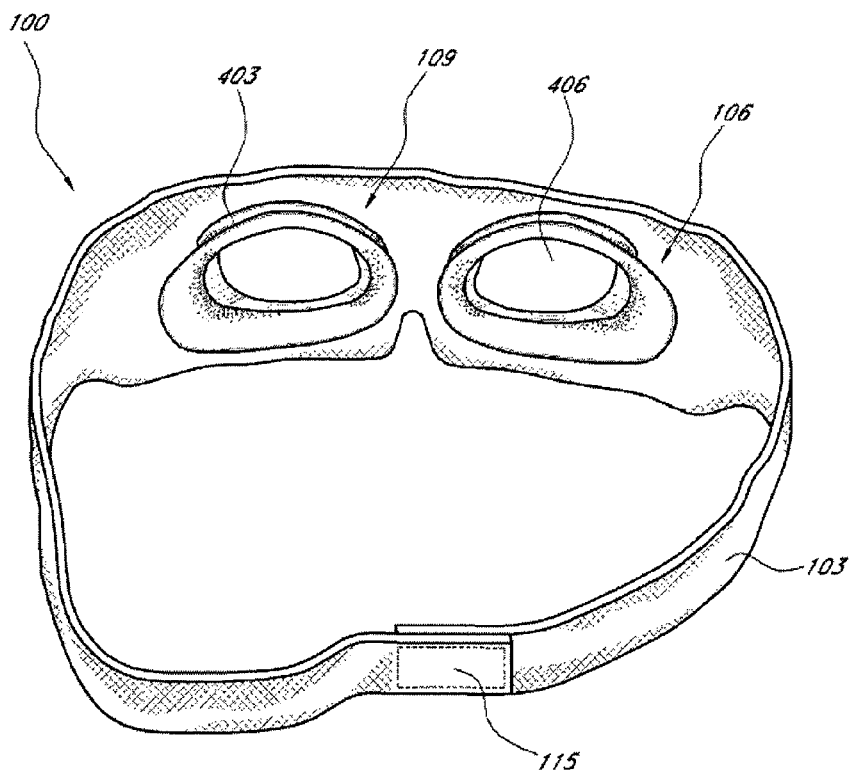
FIG. 4A is a rear perspective view of an example eye cover comprising two eye chambers.

As shown in greater detail in FIG. 4A, in certain embodiments, an eye chamber 106 comprises a flange 403 that extends from a surface of the headband 103. In certain embodiments, the flange 403 is rigid and fits snugly into the eye socket. However, the flange 403 can be resilient, flexible, or soft-walled. A resilient, flexible, or soft-walled construction advantageously permits the flange 403 to engage and conform to the wearer's face and/or eyes. A flexible construction can advantageously provide a comfortable fit for the wearer, for example, by molding to the wearer's face.

In various embodiments, the flange 403 is configured to provide in use a waterproof and/or watertight seal. For instance, a flange 403 with a flexible construction can permit a wearer to push one or more of the eye chambers toward the face. By pushing on the flexible flange, air is evacuated under the eye chamber. The pressure of the space under the eye chamber (that is, the pressure proximal the eyes) becomes lower than the pressure outside the eye chamber, thereby promoting a watertight seal. The seal created by the flange is reinforced by the positive pressure created by the headband 103. When the headband 103 is stretched around the head, the headband 103 applies pressure around the entire flange. Because the headband 103 surrounds and presses on the flange in use, additional positive pressure is exerted upon the flange, promoting a water-tight fit.

In certain embodiments, the flange 403 comprises an expanded elastomer or a plastic. In certain embodiments, the flange 403 comprises polycarbonate, Lexan, or natural or synthetic rubber. In certain embodiments, the flange 403 construction material is selected to deform to fit the face and/or eyes. In certain embodiment, the flange 403 construction material is selected to resist deterioration by chlorine or other chemical in water. In certain embodiments, the flange 403 construction material(s) can be selected to be opaque to light or selected to substantially reduce the amount of light that can pass to the wearer's eye in use, advantageously blocking extraneous light which permeates through the headband 103.

The eye chamber 106 can optionally comprise a lens 406 configured to cover the flange 403. A lens is defined as a rigid or semi-rigid cover. The lens 406 is preferably positioned in use at least over one or both eyes. Certain embodiments disclosed herein include the realization that a rigid or semi-rigid lens 406 can prevent the flange 403 (such as a flexible flange 403) from collapsing, advantageously preventing a potentially dangerous amount of suction from being exerted upon a wearer's eye. Certain embodiments disclosed herein include that realization that a rigid or semi-rigid lens 406 can be adapted to protect the wearer's eyes from impact, for example, by a wall or by another player. Because a blindfolded wearer has no vision and a compromised ability to sense obstacles, a rigid or semi-rigid lens 406 can thus advantageously improve the wearer's safety.

The lens 406 can be constructed from a waterproof material. A waterproof lens 406 can ensure a watertight and/or waterproof fit around the eyes.

The lens 406 can be attached, molded, embedded, integrated, glued, or otherwise formed to a flange. For example, a lens 406 can be heat molded to the flange. In some embodiments, the lens 406 and the flange can be a unitary construction.

Alternatively, the lens 406 can be attached, molded, embedded, integrated, sewn, or otherwise formed to the headband 103. For example, the lens 406 portion of the eye chamber 106 can be glued to the headband 103.

Preferably, the lens 406 is manufactured from a material such as polycarbonate, Lexan, silicone, safety glass, or natural or synthetic rubber. These materials (and others) can advantageously resist shattering upon impact. In certain embodiments, the material can be selected to be opaque to light or selected to substantially reduce the amount of light that can pass to the wearer's eye in use. This can advantageously reduce or block extraneous light which permeates through the headband 103, improving the action of the eye cover as a blindfold.

Figure 4B:
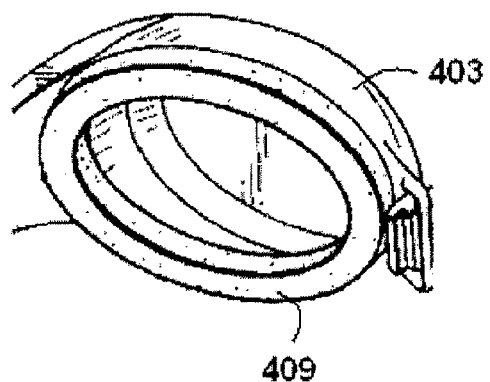
FIG. 4B is a rear perspective view of an example eye chamber comprising a flange and a gasket.

In various embodiments, an eye chamber further comprises a gasket portion disposed on at least a portion of the flange that in use contacts the face and/or eyes. An example eye chamber 109 comprising a flange 403 and gasket 409 is shown in FIG. 4B. The gasket 409 can provide and/or reinforce a watertight seal. For example, a gasket 409 can be configured to prevent the passage of air or water through gaps between the flange 403 and the wearer's face. The gasket 409 can be, for example, a resilient cushion such as a soft, low-density elastomeric pad, a closed-cell foam, a plastic cushion containing a fluid or gas, or the like. Preferably, the gasket 409 comprises a waterproof material. In certain embodiments, the gasket 409 construction material is selected to resist deterioration by chlorine and/or to improve the wearer's comfort.

Figure 5E:
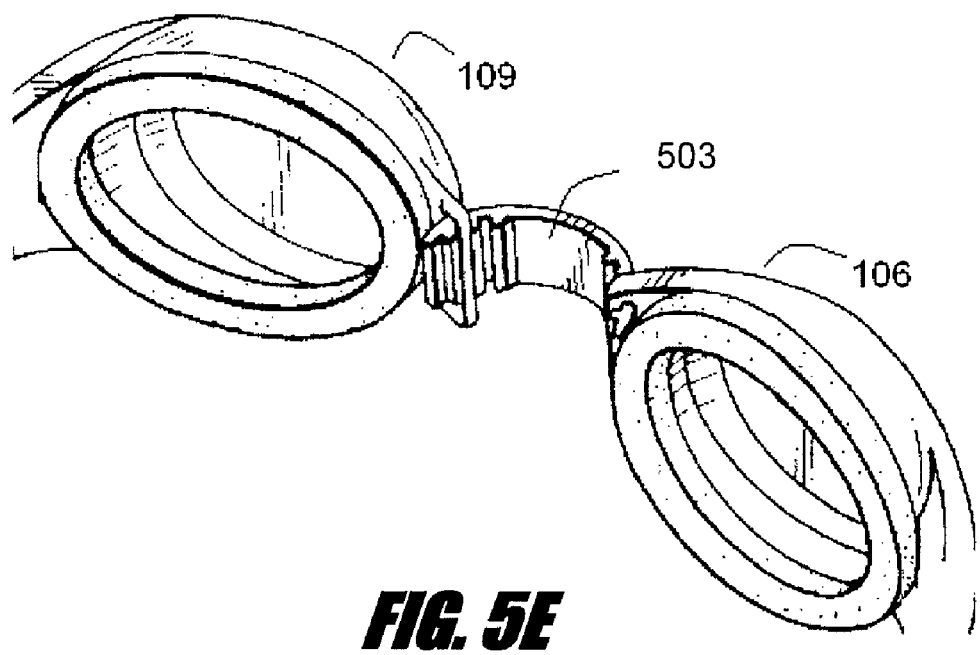

Referring to FIG. 5A, in certain embodiments, a bridge 503 can be provided between the eye chambers 106, 109. A bridge 503 can advantageously facilitate positioning the eye chambers 106, 109 on the headband 103 during construction of an eye cover. The bridge 503 can be fixedly engaged with the eye chambers 106, 109. Alternatively, as shown in FIG. 5B, the bridge 503 can be configured to permit a wearer to adjust the position of the eye chambers 106, 109 on the bridge 503 to allow a comfortable distance between the eye chambers 106, 109. FIG. 5E shows an example embodiment wherein the bridge 503 comprises grooves that are compliant with notches in the eye chambers 106, 109. A wearer can adjust and engage the notch for each eye chamber into a compliant groove in the bridge to provide a comfortable distance between the eye chambers. An adjustable bridge-and-chamber configuration can advantageously provide a customizable fit that prevents the eye chambers from shifting off the wearer's eyes in use.

Figure 6A:
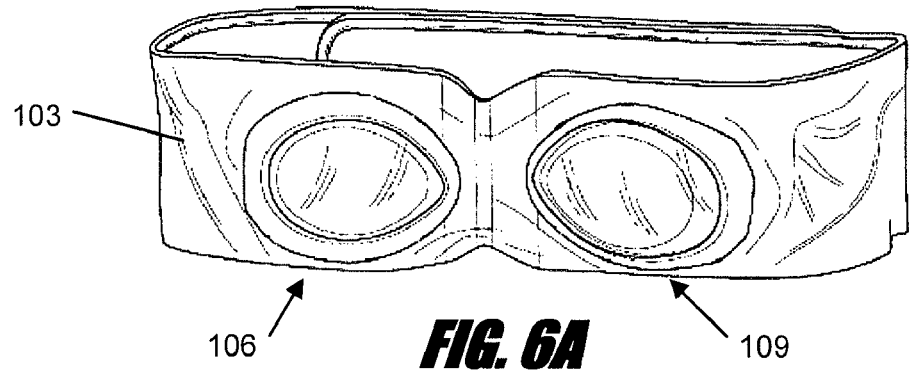
FIG. 6A through FIG. 6C show an example eye cover comprises two eye chambers, wherein the eye chambers are inserted through a headband.
Figure 6B:
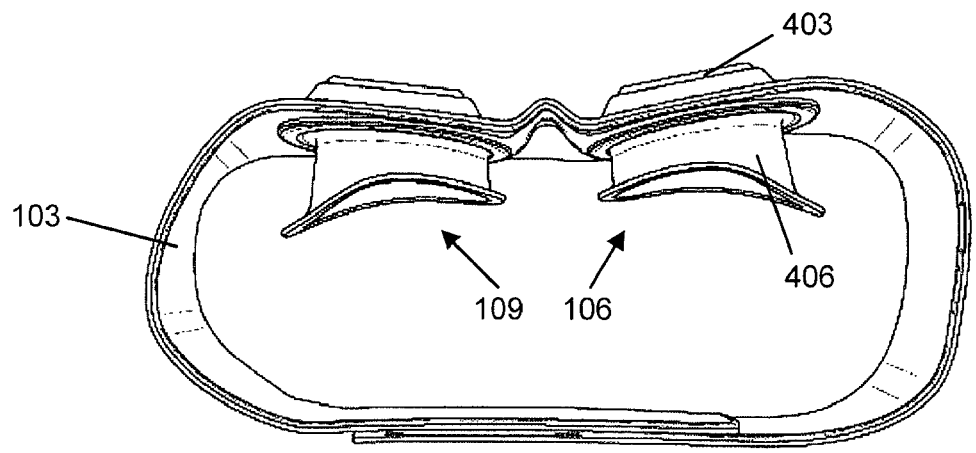
Figure 6C:
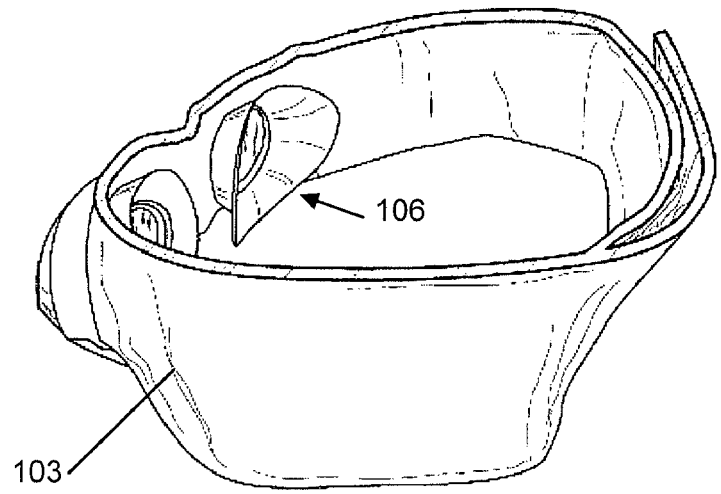

Referring to FIG. 6A, in certain embodiments, the headband 103 can comprise one or two cutout regions. One or two eye chambers 106, 109 can be inserted through the cutout regions or disposed over the cutout regions. Suitable methods for securing the one or two eye chambers 106, 109 to the headband 103 are described above, such as heat molding, stitching, gluing, and the like. Alternative views of the eye cover 100 of FIG. 6A are shown in FIG. 6B and FIG. 6C. The one or two eye chambers 106, 109 are configured in use to cover the wearer's eyes. As shown in FIG. 6B, each of the one or two eye chambers 106, 109 comprises a lens 403 and a flange 406. As explained above, the one or two eye chambers 106, 109 can form in use a watertight seal around the wearer's eyes. In the example embodiment of FIG. 6A, the headband 103 is configured to be wrapped around the wearer's head. As an alternative, however, the headband 103 can be configured to be pulled around the wearer's head, such that the headband 103 is positioned over the wearer's eyes. The lenses shown 403, 406 in FIG. 6B are preferably transparent. That is, the wearer is able to see through the lenses 403 to clearly discern images. Nevertheless, the lenses 403 can also be opaque or configured to obscure images in various embodiments.

One or more shaped shells can be provided on a surface of the headband 103 that in use faces outward. Preferably, the one or more shells are rigid or semi-rigid. A rigid shell is inflexible. A semi-rigid shell is sufficiently stiff to maintain a certain shape and to return to the shape after deformation. In certain embodiments, a wearer can grasp at least one of the one or more shells to facilitate removal of the headband 103. Referring to FIG. 7A, in one embodiment, two substantially hemispherical shells 703, 706 are provided on the portion of the headband 103 proximal the wearer's eyes. Referring to FIG. 7B, two cat-eye shaped shells 709, 712 are provided on a portion of the headband 103 proximal the wearer's eyes. The outer surface of the one or more shells can be decorated, for example, to resemble fly eyes, animal eyes, or other shapes. In various embodiments, the one or more shells can be made of one or more materials such as foam, rubber, plastic, etc. The one or more shells can be attached, molded, embedded, integrated, glued, sewn, or otherwise formed to the headband 103. In various embodiments, the one or more shells and the headband 103 are a unitary construction. For example, during manufacture of a neoprene headband 103, one or more shells in the headband 103 can be molded into shape.

Figure 8B:
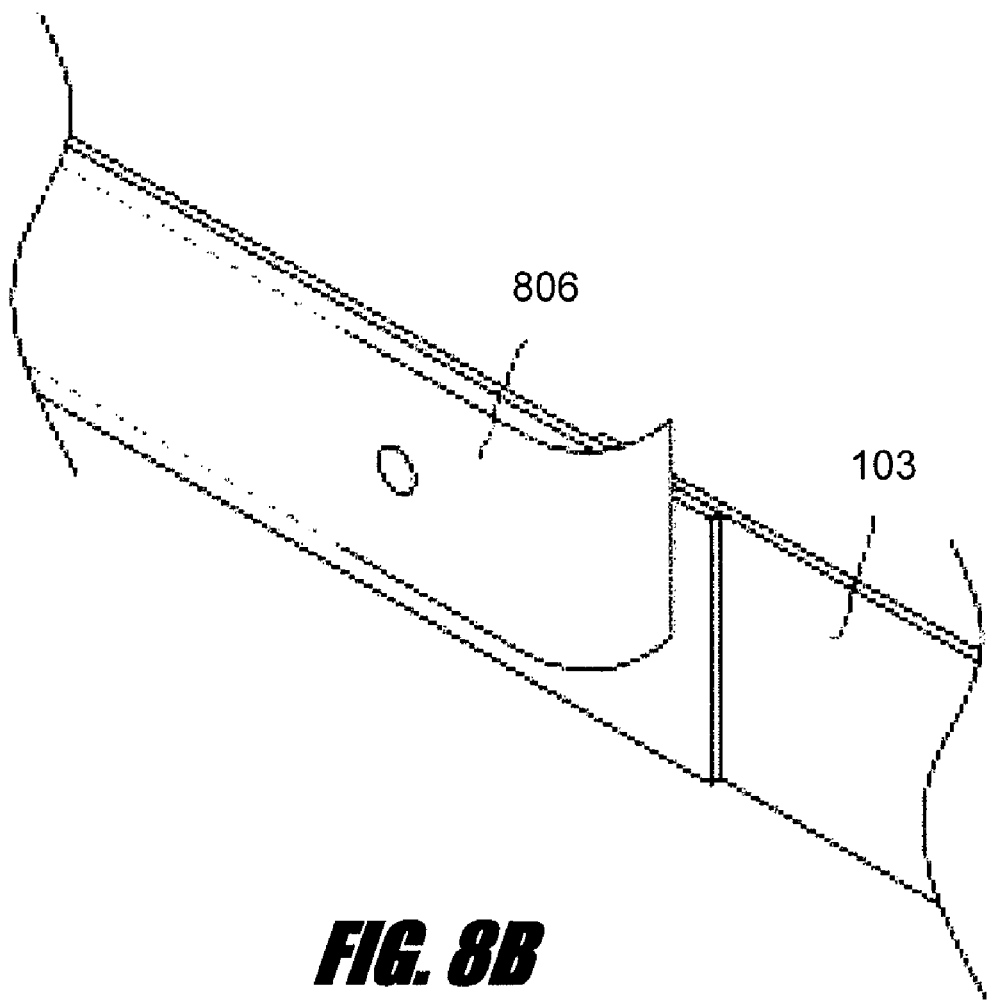
FIG. 8B is a rear perspective view of another example eye cover comprising a handle.

In various embodiments, one or more handles can be provided on a surface of the headband 103 that in use faces outward. Preferably, the one or more handles are rigid (that is, inflexible) or semi-rigid. Referring to FIG. 8A, at least one handle can, for example, resemble a bumper, visor, or bar 803 disposed on a portion of the headband 103 above the wearer's eyes. In alternative embodiments, the at least one handle can be disposed on a portion of the headband 103 near the wearer's ears, nose, etc. In one embodiment, the handle is a visor about 4 inches long (horizontally), about 1½ to 2 inches deep, and about ¼ to ¾ inch in thickness. Referring to FIG. 8B, at least one handle can comprise a tab or bar 806 disposed on the headband 103, such as near an edge of the headband 103. In certain embodiments, a wearer can grasp, pull, or bump at least one of the one or more handles to facilitate removal of the headband 103. In various embodiments, the one or more handles can be made of one or more materials such as foam, rubber, plastic, etc.

Figure 9A:
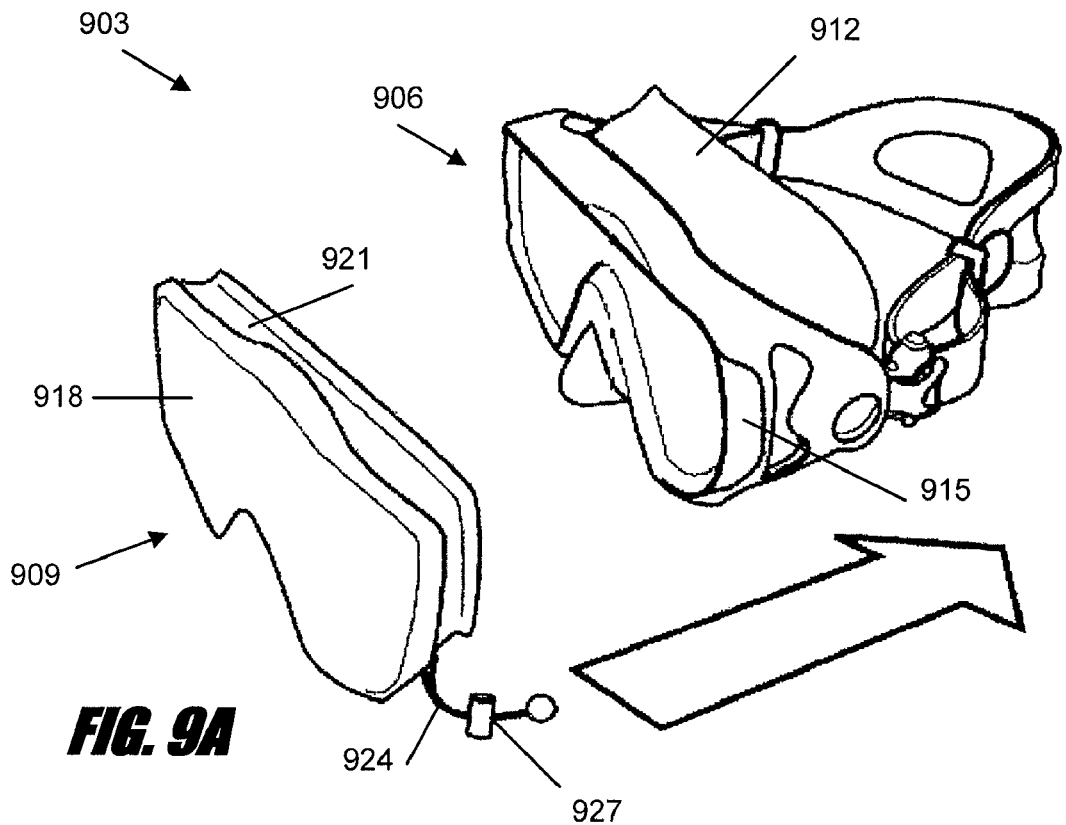
FIG. 9A and FIG. 9B show an eye cover comprising a covering system and an overlay configured to cover at least a portion of the covering system.

As shown in FIG. 9A, in various embodiments, an eye cover 903 is provided comprising an covering system 906 (e.g., comprising swim goggles or a swim mask 912) and an overlay 909 configured to cover at least a portion of the covering system 906. Preferably, the overlay 909 can be removably engaged with the covering system 906. Such embodiments are advantageous because they allow the overlay 909 to be traded among wearers (e.g., playing blind tag or Marco Polo). However, the overlay 909 can also be permanently engaged over the covering system 906 in some embodiments.

In some embodiments, the covering system 906 comprises a projecting portion 915 that projects outward from the swim goggles or swim mask 912. The projecting portion 915 can advantageously facilitate engaging the overlay 909 on the covering system 906. The projecting portion 915 can be disposed, for example, on side of the covering system 906, as shown in FIG. 9A, around the perimeter of the front viewing portion of the swim mask 912, etc.

Figure 9B:
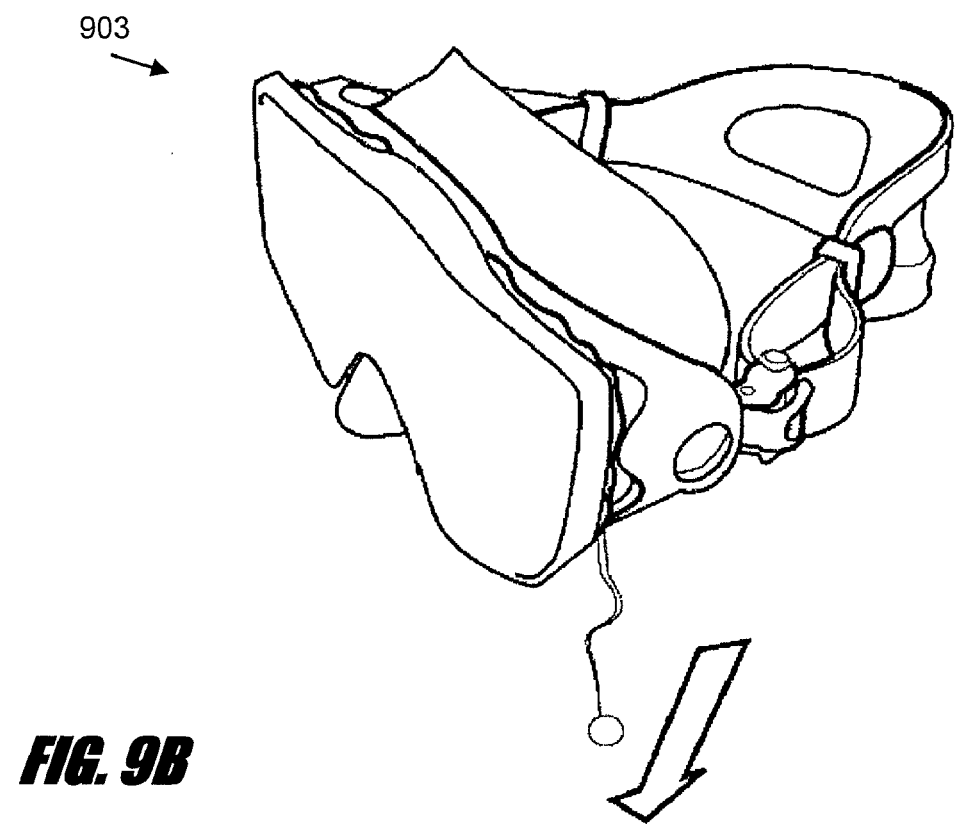

The overlay 909 can comprise a skirt 918 or other suitable means for covering the covering system 906. In the example embodiment of FIG. 9A, the skirt 918 comprises a perimeter portion 921. A cord 924 can be disposed within the perimeter portion 921. A fixing mechanism 927 (shown in FIG. 9A as a barrel lock) is disposed on the cord 924. The fixing mechanism 927 is configured to slide up and down along the cord 924 and engage in a fixed location. By sliding the fixing mechanism 927 up along the cord 924 and affixing the fixing mechanism 927 in place, the effective circumference of the cord 924 is decreased. Conversely, by sliding the fixing mechanism 927 down along the cord, the effective circumference of the cord 924 is increased. FIG. 9B shows the overlay 909 when it is removably engaged with the covering system 906.

As demonstrated by the example embodiment of FIG. 9A, a method of removably engaging the overlay 909 with the covering system 906 is provided. The perimeter portion 921 of the skirt 918 is pulled around the projecting portion 915. The fixing mechanism 927 slides up along the cord 924 and affixes in place to ensure that the cord 924 fits snugly around the perimeter portion 921. To remove the overlay 909 from the covering system 906, the fixing mechanism 927 is loosened by sliding it down along the cord 924. When the fixing mechanism 927 is loosened, the cord 924 is slack around the perimeter portion 921. Accordingly, the overlay 909 can be easily disengaged from the covering system 906.

Of course a wide variety of alternative methods for covering the covering system 906 are suitable. For example, an elastic band can be disposed within the perimeter portion 921 of the skirt 918 instead of (or in conjunction with) the cord 924. As another example, in certain embodiments, a portion on the headband (as described above) that covers the eye chambers is absent or removable. For example, a removable portion can be attached to a headband with Velcro strips. When a player is It, the removable portion covers the It player's eye chambers. When the It player tags another player, the It player removes the removable portion and transfers it to the tagged player. The tagged player can then apply the Velcro to compliant strips on the tagged player's headband. In embodiments comprising an absent or removable portion, the eye chambers preferably comprise translucent, rigid or semi-rigid lids. The positive pressure of the stretchy headband exerted on the flange and/or gasket can advantageously provide an improved sealing goggle with a wide strap for comfort.

While certain embodiments of the inventions have been described, these embodiments have been presented by way of example only, and are not intended to limit the scope of the inventions. Indeed, the novel methods and systems described herein can be embodied in a variety of other forms. For example, although described primarily in the context of blind tag variants, the above watertight eye cover can be used in other swimming events. In Paralympic-affiliated events, swimmers who compete under the S11 classification (that is, visually impaired with little or no sight) are required to wear opaque or blackened goggles during competition. The watertight eye covers described herein can provide a hydrodynamic alternative blindfold for competitions. Moreover, various embodiments disclosed herein are suitable for sighted swimming and game play. Adaptations and modifications are within the meaning and range of equivalents of the disclosed embodiments. The phraseology or terminology employed herein is for the purpose of description and not of limitation. Furthermore, various omissions, substitutions and changes in the form of the methods and systems described herein can be made without departing from the spirit of the inventions. The accompanying claims and their equivalents are intended to cover such forms or modifications as would fall within the scope and spirit of the inventions.

What is claimed is:

1. A blindfold for use in an aquatic environment to cover a wearer's eyes, comprising:
    an elastic headband, wherein the elastic headband is configured in use to be worn around the wearer's head, to cover the wearer's eyes as a blindfold,
    the headband having a one-piece construction of a substantially opaque material and configured to provide a blindfold for the wearer, the headband material being planar and continuous on its outward facing surface in the vicinity of the wearer's eyes and without cutouts or openings for eyes or lenses, the headband having a substantially rectangular configuration along its entire length when laid out on a planar surface and being configured to be wide enough to cover above and below the eyes and along the temples of the wearer when applied to the wearer,
    the headband having an upper longitudinal edge and a lower longitudinal edge, the lower longitudinal edge having a cut-out for the wearer's nose, the headband material being stretchy and forming a watertight seal around the wearer's eyes where it touches the face of the wearer,
    the headband having an outward facing surface facing away from the wearer and an inward facing surface facing toward the face of the wearer when the headband is in place on the wearer's head; and
    at least one eye chamber comprising an eye cup and forming a concave space configured to allow the eye of the wearer to be open during use, the at least one eye chamber being disposed on the inward facing surface of the headband that in use faces the wearer's eyes, the at least one eye chamber being configured in use to provide at least a watertight seal around the wearer's eye, wherein the at least one eye chamber, comprises:
    a flange having a planar portion and a side wall portion, the planar portion configured to mount the flange to the inward facing surface of the headband, the flange extending peripherally around the eye chamber and the flange side wall extending inwardly from the inward facing surface of the headband; and
    a gasket on the flange and being configured to engage the face of the wearer and be deformable such that manual pressure can be applied to the gasket to evacuate air from the eye socket of the wearer,
    the flange of the at least one eye chamber further being substantially rigid and substantially opaque and disposed on the inward facing surface of the headband such that in use the flange faces the wearer's eyes, the flange providing protection for the eyes of the wearer and further preventing the wearer from seeing through the blindfold, and
    the width of the headband being greater than the width of the at least one eye chamber to provide stability and water-resistance during swimming and aquatic games.

2. The blindfold of claim 1, wherein the headband is secured around the wearer's head by hook and loop fabric, a snap, or a grommet.

3. The blindfold of claim 1, wherein the headband comprises a sealing fabric or material that is configured to provide an additional seal around the wearer's eyes, wherein the additional seal is at least a water-resistant seal.

4. The blindfold of claim 3, wherein the sealing fabric or material is neoprene, plastic, or vinyl.

5. The blindfold of claim 1, wherein the headband comprises at least one sealing structure disposed on the inward facing surface of the headband that in use faces the wearer's eyes, wherein the sealing structure is configured to provide an additional seal around the wearer's eyes, wherein the additional seal is at least a water-resistant seal.

6. The blindfold of claim 5, wherein the sealing structure comprises a waterproof bead or strip.

7. The blindfold of claim 1, further comprising one or more rigid or semi-rigid projections disposed on the outward facing surface of the headband, configured to facilitate removal of the headband.

* * * * *